United States Patent
Yang et al.

(10) Patent No.: US 9,458,421 B2
(45) Date of Patent: Oct. 4, 2016

(54) **CULTURE METHOD FOR *ANTRODIA CINNAMOMEA***

(71) Applicants: Tunghai University, Taichung (TW); Greenyn Biotechnology Co., Ltd, Taichung (TW)

(72) Inventors: Fan-Chiang Yang, Taichung (TW); Chia-Li Wu, Taichung (TW); Ya-Chen Chi, Taichung (TW)

(73) Assignees: TUNGHAI UNIVERSITY, Taichung (TW); GREENYN BIOTECHNOLOGY CO., LTD., Taichung (TW)

( * ) Notice: Subject to any disclaimer, the term of this patent is extended or adjusted under 35 U.S.C. 154(b) by 397 days.

(21) Appl. No.: 14/147,780

(22) Filed: Jan. 6, 2014

(65) Prior Publication Data
US 2015/0052639 A1    Feb. 19, 2015

(30) Foreign Application Priority Data
Aug. 19, 2013    (TW) .............................. 102129661 A (51) Int. Cl.
*C12N 5/00*    (2006.01)
*C12N 5/02*    (2006.01)
*C12N 1/14*    (2006.01)
*C12N 13/00*    (2006.01)

(52) U.S. Cl.
CPC ................. *C12N 1/14* (2013.01); *C12N 13/00* (2013.01)

(58) Field of Classification Search
CPC ............................... A01G 1/04; A01G 1/044
USPC ....................... 435/420, 256.8, 254.1; 47/1.1
See application file for complete search history.

(56) References Cited

U.S. PATENT DOCUMENTS 7,971,388 B2 *   7/2011   Kawai .................... A01G 1/044
                                                        47/1.1
8,524,486 B2 *   9/2013   Tsai ......................... A01G 1/04
                                                        435/254.1

\* cited by examiner

*Primary Examiner* — Kent L Bell
(74) *Attorney, Agent, or Firm* — Ming Chow; Sinorica, LLC (57) ABSTRACT

The invention discloses a culture method for *Antrodia cinnamomea* to elevate the amounts and types of the bioactive components in *Antrodia cinnamomea* through controlling the wavelength and intensity of the light. Furthermore, the modification of the environmental factors such as water content, composition and relative amount of the culture medium, and the culture temperature are capable of increasing the amounts and types of the bioactive components in *Antrodia cinnamomea*.

18 Claims, 7 Drawing Sheets

CULTURE METHOD FOR *ANTRODIA CINNAMOMEA*

The current application claims a foreign priority to the patent application of Taiwan No. 102129661 filed on Aug. 19, 2013.

FIELD OF THE INVENTION

The present invention relates to a culture method for fungal. Especially, the present invention relates to a culture method for *Antrodia cinnamomea*.

BACKGROUND OF THE INVENTION

*Antrodia cinnamomea* is a native fungal species in Taiwan and growing inside the decayed heart-wood of *Cinnamonum kanehirae* that distributes in the mountains with 450 to 1500 meters above sea level in Taiwan. The current reports have suggested that *Antrodia cinnamomea* contains extremely high nutritional value resulted from various physiological properties of the containing bioactive components. Therefore, *Antrodia cinnamomea* is a precious fungal species with growing demand in the market. Furthermore, the major bioactive components in *Antrodia cinnamomea* include the polysaccharides, polyphenols and major indicative product, triterpene. Herein, the previous reports show that polysaccharides contain the functional properties in strengthening immunity and anti-cancer. In the organism, polyphenols play the role as reductant for anti-oxidation by removing the free radicals and inhibiting the oxidation of LDL-cholesterol. In addition, polyphenols are capable of suppressing tumor growth through inhibition of enzymes activities that are required for tumor growth. Furthermore, triterpene contain the functions in promoting cancer cell death, suppressing proliferation of hepatoma, participating the hepatic repair, strengthening hepatic functions, anti-inflammation, lowering blood lipid, reducing blood pressure, preventing apoplexy and modulating immunity. However, *Antrodia cinnamomea* is growing inside *Cinnamonum kanehirae*, which is a protected species with slowly growing rate. It is difficult to acquire enough amount of *Antrodia cinnamomea* from the native environment for the demand in the market. Therefore, the developing approaches to acquire more *Antrodia cinnamomea* and efficiently increase the amounts of bioactive components in *Antrodia cinnamomea* are important issues for the current biomedical industry.

In the practical culture methods, the acquired bioactive components from *Antrodia cinnamomea* are dependent on the conditions of culture methods. Recently, the common culture methods for *Antrodia cinnamomea* include liquid-state culture, solid-state culture and Basswood culture. In liquid-state culture method, *Antrodia cinnamomea* is cultured in the liquid-state medium with appropriate carbon/nitrogen ratio. Liquid-state culture method contains the advantages such as low cost and short culture time requirement that spends 7~14 days for complete culture. However, the liquid-state culture method for *Antrodia cinnamomea* exhibits low concentration of triterpene which is different to that in wild *Antrodia cinnamomea*.

In solid-state culture method, *Antrodia cinnamomea* is cultured on the solid-state culture medium that is composed of cereals and water. The *Antrodia cinnamomea* cultured by solid-state culture method contains higher concentration of triterpene through artificial regulations of temperature and humidity. However, solid-state culture method for *Antrodia cinnamomea* requires longer culture time that spends 3~6 months. Furthermore, the manufactural quality is inconsistent due to different compositions of bioactive components in the *Antrodia cinnamomea* cultured on different solid-state medium. In addition, the triterpene produced in the cultured *Antrodia cinnamomea* cannot include all effective forms of triterpene in wild *Antrodia cinnamomea*.

In Basswood culture, *Antrodia cinnamomea* cultured inside the trunk of *Cinnamonum kanehirae* bears the same components as that in the fruiting body of wild *Antrodia cinnamomea*. Assisting with modifications of culture conditions, Basswood culture is capable of providing the stable quality of fruiting body in *Antrodia cinnamomea*. However, it spends 1~3 years to obtain the mature *Antrodia cinnamomea* by Basswood culture method. Furthermore, *Cinnamonum kanehirae* is a protective species that limits the source of culture medium base and makes it difficult in manufacture due to the expansive cost.

Currently, solid-state culture method is the most common culture method for *Antrodia kanehirae* to give consideration to production of bioactive components and manufacture cost. However, some defects still remain in the current culture technologies. For example, the separation of cultured *Antrodia cinnamomea* and the solid-state medium is difficult to be achieved. The products contaminated with some medium will limit the further applications of the cultured *Antrodia cinnamomea*. Furthermore, the fruiting body of the solid-state cultured *Antrodia cinnamomea* is thinner so it contains less bioactive components than the wild *Antrodia cinnamomea*. Furthermore, by modifications of the culture light in the liquid-state culture method, it will affect the amounts of the bioactive components in *Antrodia cinnamomea*. For example, while *Antrodia cinnamomea* is cultured under the blue light, it increases the amount of extracellular polysaccharides but not triterpene. In contrast, while *Antrodia cinnamomea* is cultured under the red light, it elevates the amounts of triterpene but not extracellular polysaccharides. Therefore, there is not ideal culture method for *Antrodia cinnamomea* to elevate the amounts of bioactive components with the acceptable cost.

SUMMARY OF THE INVENTION

The main aspect of the present invention provides a culture method for *Antrodia cinnamomea* that can use for elevating the amounts and types of the bioactive components.

The present invention discloses the culture method for *Antrodia cinnamomea* that inoculates a seed strain of *Antrodia cinnamomea* to a culture medium with at least one culture condition, wherein the culture condition including a light environment which is green light or blue light.

Furthermore, the light intensity of the light environment is between 1 $\mu$mol/s·m$^2$ to 20 $\mu$mol/s·m$^2$. In one embodiment the intensity of the blue light is between 2 $\mu$mol/s·m$^2$ to 16 $\mu$mol/s·m$^2$, and in the other embodiment, the intensity of the green light is between 11 $\mu$mol/s·m$^2$ to 20 $\mu$mol/s·m$^2$.

The culture condition is further including a culture temperature that is between 25° C.~35° C. In addition, the culture medium includes a powder matrix and water, wherein the powder matrix has at least one cereal grain such as Tartary buckwheat flour, brown rice powder, adlay powder or at least two foresaid powders mixed in a predetermined ratios.

In some embodiments, the powder matrix is mixed of Tartary buckwheat flour, brown rice powder and adlay powder, wherein in one embodiment, the contained amount of the powder matrix from low to high is sequentially adlay powder, Tartary buckwheat and brown rice powder; in another embodiment, the contained amount of the powder matrix from low to high is sequentially adlay powder, brown rice powder Tartary buckwheat flour. In one embodiments, the mixed ratio of the powder matrix is 1-fold adlay powder, 10- to 2-fold brown rice powder and 2~10 folds of Tartary buckwheat flour. In another embodiment, the ratio of brown rice powder, Tartary buckwheat flour and adlay powder in the powder matrix is 9:2:1.

Moreover, the water content of the culture medium is between 35~55% wherein the water content is between 35~50% of the culture medium for containing more bioactive components in *Antrodia cinnamomea*.

The seed strain is prepared by homogenization of *Antrodia cinnamomea* mycelia. It is used for making the *Antrodia cinnamomea* mycelia be homogeneous under visible state to inoculate conveniently and avoid contamination.

Moreover, the culture method of the invention includes two culture conditions, wherein one culture condition is to culture the *Antrodia cinnamomea* in dark environment for 15 days and another culture condition is to culture the *Antrodia cinnamomea* in light environment at least for 15 days. In one embodiment, the culture temperature of the culture condition is lower than that of another the culture condition. Practically, the culture temperature of the culture condition is 25° C., and the culture temperature of another the culture condition is between 25~35° C.

According to the culture method for *Antrodia cinnamomea* disclosed in the invention, it will elevate the amounts and types of the bioactive components in the cultured *Antrodia cinnamomea*. Also, it could lower the cost of culturing *Antrodia cinnamomea* for large-scale production and being the raw materials for industrial applications. In other words, it improves the economic value of *Antrodia cinnamomea*.

DETAILED DESCRIPTION OF THE INVENTION

In the invention, the culture method for *Antrodia cinnamomea* can enrich the amounts and types of the bioactive components in the cultured *Antrodia cinnamomea* through changing the light wavelength of the light environment. Furthermore, modifications of the culture condition, such as water content of the culture medium, compositions of the culture medium and the mixed ratio thereof, culture temperature or other environmental factors, would further elevate the amounts and types of the bioactive components in *Antrodia cinnamomea*.

Unless defined otherwise, all technical and scientific terms used herein have the same meanings commonly understood by one of ordinary skill in the art. As used in this application, including claims and specification, the following words is only exemplary and illustrative, not limiting in scope.

The term of culture medium includes the liquid-state and solid-state mediums for culturing fungi.

The term of cereal grain indicates rice, broom coin millet, millet, wheat, beans and nuts, such as brown rice, rice, coarse rice, corn, wheat, Italian millet, sorghum, oats, barley, buckwheat, soybean, mung bean, azuki bean, red bean, black bean, walnut, adlay, and pumpkin seed.

To understand the purposes and advantages of the present invention, it is described by the following merely examples taken in conjunction with the accompanying drawings. It will be understood that it is not intended to limit the invention to the described embodiments.

Example 1

Preparation of the Seed Strain

The seed strain of *Antrodia cinnamomea* (Catalog number BCRC35396) was acquired from Bioresource Collection and Research Center (BCRC) in Food Industry Research and Development Institute, ShinChu, Taiwan. The *Antrodia cinnamomea* was cultured in the slant culture medium at 25° C. until the mycelia of *Antrodia cinnamomea* occupy the whole medium, wherein the slant culture medium is composed of 2% of glucose, 2% of malt extract, 0.1% of Peptone and 2% Agar.

The appropriate mycelia of *Antrodia cinnamomea* were aliquoted from the slant culture medium onto the plate medium in Petri dish for the further culture until the colony reached 3.5 cm in radius, and then the plate medium was divided the plate medium into eight equal fragments, wherein the plate medium in the Petri dish contains the same constitute as the slant culture medium.

Each fragment of the plate medium was put into a bottle of liquid-state medium and then was homogenized for the following culture in the incubator at 25° C., 100 rpm for 5 days. The product of the liquid-state culture is used for the following examples, wherein the liquid-state medium comprises 2% glucose, 2% malt extract and 0.1% Pepton

Example 2

Measurement of the Intracellular Polysaccharides

The centrifuge tube with 100 mg powder of a sample and 10 ml distilled water is autoclaved and then centrifuged at 8000 rpm for 5 minutes. After the centrifugation, the supernatant is collected and mixed with 95% ethanol in the ratio 1:4. The mixture is incubated at 4° C. for 24 hours to precipitate the polysaccharides existing in the aqueous layer. Following the precipitation, the mixture is further centrifuged at 8000 rpm for 5 minutes to separate the supernatant and precipitate. After removing the supernatant, the precipitate is dissolved in NaOH solution for measuring the intracellular polysaccharides by Phenol-sulfuric acid assay. By the Phenol-sulfuric acid assay, the diluted samples are sequentially added with 1 ml of 5% phenol and 5 ml sulfuric acid that is mixed for 10 minutes. The mixture is further incubated in water-bath at 25° C. for 15 minutes and analyzed the absorption of 490 nm wavelength using spectrophotometer to determine the concentration of the polysaccharides in the sample.

Example 3

Detection of the Total Amount of Polyphenols

Taking the fruiting body of a sample with methanol in the ratio 1:20, that is proceeding extraction in the water-bath at 50° C. with shacking at 130 rpm for 12 hours and then centrifuged at 8000 rpm for 5 minutes to obtain the supernatant. The collected supernatant is mixed well with 6 ml of 2% $Na_2CO_3$, and then added the Folin-Clocalteu's phenol reagent for 30 minutes. The concentration of polyphenols is determined by measuring the absorption of 730 nm wavelength. The concentration of total amount of polyphenols is calculated by comparing to the standard curve determined by gallic acid with known concentrations.

Example 4

Detection of the Amount of Triterpene

In a centrifuge tube, 100 mg sample is mixed well with 3 ml of 50% ethanol by sonication for 30 minutes that is followed by centrifugation at 8000 rpm for 5 minutes and then collected 3 ml supernatant in a sample bottle. Repeated to the above procedures include addition of ethanol into the centrifuge tube, extraction and centrifugation. After the centrifugation, 3 ml supernatant is collected and transferred into the sample bottle.

The collected supernatant in the sample bottle is dried and re-dissoluted with 3 ml water and 3 ml chloroform that is followed by sonication for 30 minutes to collect the bottom layer in the sample bottle. The bottom layer is mixed with 3 ml of 5% $NaHCO_3$ by sonication for 30 minutes. After sonication, the pH value of the bottom layer is adjusted to 2~3 and then collected the bottom solution from the bottom layer. The bottom solution is dried by heat, and then re-dissoluted with 2 ml saturated ethanol for analysis of the amount of triterpene in the sample by detecting the absorption of 245 nm wavelength.

Example 5

The Effects of the Wavelength and Intensity of the Light

The brown rice was grained into powder by rollermill. First, 25 g of brown rice powder was mixed well with 15 g of water and sterilized to prepare the solid-state medium for *Antrodia cinnamomea*. The seed strain of *Antrodia cinnamomea* prepared in example 1 was spread on the solid-state medium with 5% inoculation rates. The medium spread with *Antrodia cinnamomea* was sealed and cultured in the incubator at 25° C. for 15 days. After 15 days, the cultured *Antrodia cinnamomea* on the solid-state medium was further treated with light.

In this example, there were two experimental groups that were treated with light of different wavelengths, wherein the experimental group 1 was treated with green light and experimental group 2 was treated with blue light. Furthermore, each experimental group was divided into 4 sub-groups that were treated with the green light or blue light with different intensity, wherein of the each experimental group, the sub-group 1 was the blank control; the sub-group 2 was treated with light intensity at 1~2 µmol/s·m²; the sub-group 3 was treated with light intensity at 15~16 µmol/s·m²; and the sub-group 4 was treated with light intensity at 19~20 µmol/s·m².

After 15 days culture with light treatments, the *Antrodia cinnamomea* growing in each sub-groups of experimental groups 1 or 2 were collected and dried for 24 hours. The dried *Antrodia cinnamomea* was grained into powder for measuring the amount of crude triterpenoids, polyphenols and intracellular polysaccharides by using the methods indicated in examples 2~4. The indicated procedures were repeated for three times to determine the amounts of these bioactive components in the cultured *Antrodia cinnamomea*. The statistic results of the measured bioactive components in *Antrodia cinnamomea* are showed in FIG. 1 and FIG. 2, wherein FIG. 1 and FIG. 2 show the statistic results of experimental group 1 and experimental group 2, respectively.

Figure 1:
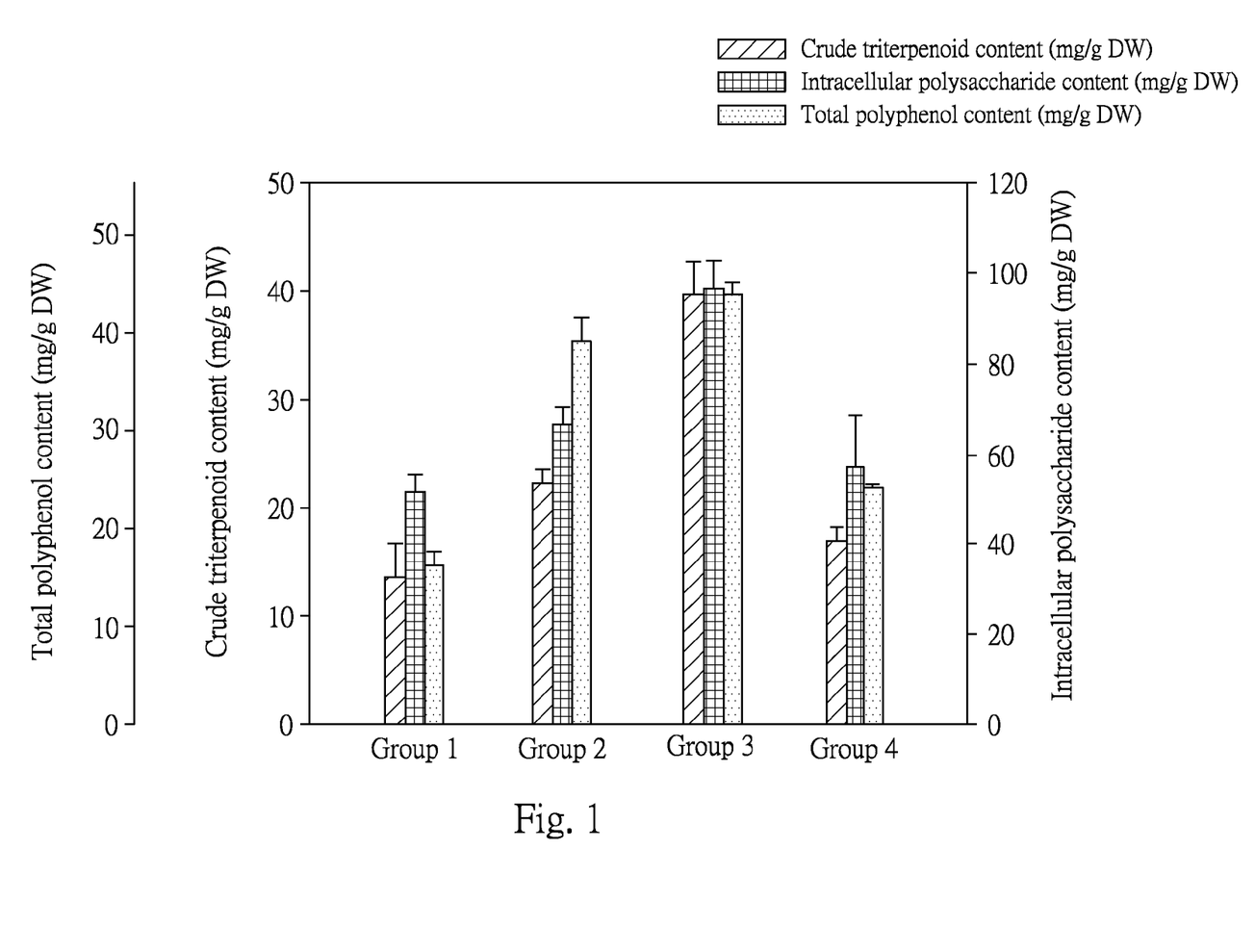
FIG. 1 is the results of the amounts of the bioactive components in the *Antrodia cinnamomes* treated with different intensity of green light.

The FIG. 1 shows that the intracellular polysaccharides in sub-group 2, 3 and 4 of experimental group 1 are 66.38 mg/g, 96.55 mg/g and 60.19 mg/g, respectively. In addition, the polyphenol of these three indicated subgroups are 38.86 mg/g, 43.71 mg/g and 25.46 mg/g; the crude triterpenoid of these three indicated sub-groups are 22.28 mg/g, 39.64 mg/g and 17.81 mg/g.

Figure 2:
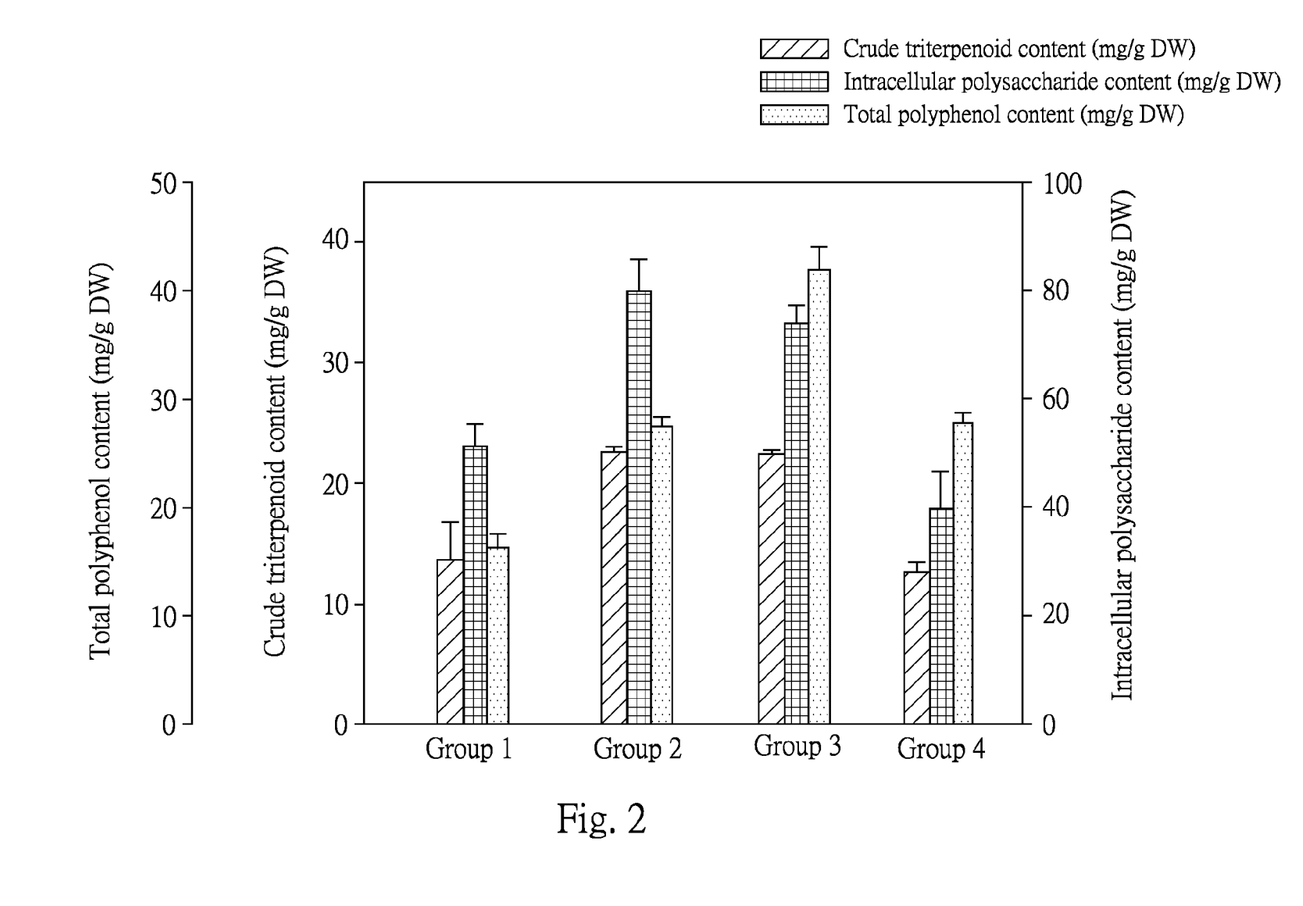
FIG. 2 is the results of the amounts of the bioactive components in the *Antrodia cinnamomes* treated with different intensity of blue light.

Furthermore, FIG. 2 shows that the intracellular polysaccharides of sub-group 2, 3 and 4 of experimental group 2 are 79.78 mg/g, 73.83 mg/g and 41.61 mg/g, respectively. In addition, the polyphenols of these indicated sub-groups are 27.46 mg/g, 41.90 mg/g and 29.09 mg/g; the crude triterpenoid of these three indicated sub-groups are 22.59 mg/g, 22.39 mg/g and 13.15 mg/g.

Moreover, the amount of polyphenols in the *Antrodia cinnamomea* cultured with treatment of green light at 15~16 µmol/s·m² reveals 2.69 folds than that of blank group; the amount of crude triterpenoid in the *Antrodia cinnamomea* treated with green light at 15~16 µmol/s·m² reveals 2.92 folds than that of blank control; and the amount of polyphenols in the *Antrodia cinnamomea* treated with blue light at 15~16 µmol/s·m² reveals 2.53 folds than that of blank control and the amount of crude triterpenoid in the *Antrodia cinnamomea* treated with blue light at 15~16 µmol/s·m² reveals 2.70 folds than that of blank control.

Therefore, the FIG. 1 and FIG. 2 show that either treatment of green light or blue light is capable of increasing the amounts and types of the bioactive components in the cultured *Antrodia cinnamomea*. Specifically, the treatment of blue light at 2~16 µmol/s·m² or green light at 11~20 µmol/s·m² results in the greatest contents of bioactive components.

Example 6

The Effects of Water Content of the Solid-State Medium

The appropriate amount of the brown rice powder was mixed with water in specific ratio to prepare the solid-state culture mediums with 55% and 45% water contents for group 1 and group 2, respectively. The seed strain of *Antrodia cinnamomea* was spread on the medium of each group with 5% inoculation rate and followed by culture for 3 months. While the culture time period reached 3 months, the growing *Antrodia cinnamomea* of each group was collected from the solid-state medium for the measurements by the indicated procedures in example 2~4 to determine the amounts of the bioactive components. The results of these measurements are showed in FIG. 3.

The Tartary buckwheat flour base medium or adlay powder based medium contain different water contents of 45% and 55% were prepared using the same procedures as the example given above and were divided into group 1 and group 2, wherein the group 1 is the culture medium of 55% water content and the group 2 is the culture medium of 45% water content The amounts of these indicated bioactive components in the cultured *Antrodia cinnamomea* of each group were measured after culturing for 3 months. The results of the measured bioactive components in the cultured *Antrodia cinnamomea* are showed in FIG. 4 and FIG. 5, wherein FIG. 4 shows the results of culturing on the Tartary buckwheat flour based medium with different water contents and FIG. 5 shows the results of culturing on the adlay powder based medium with different water contents.

Figure 3:
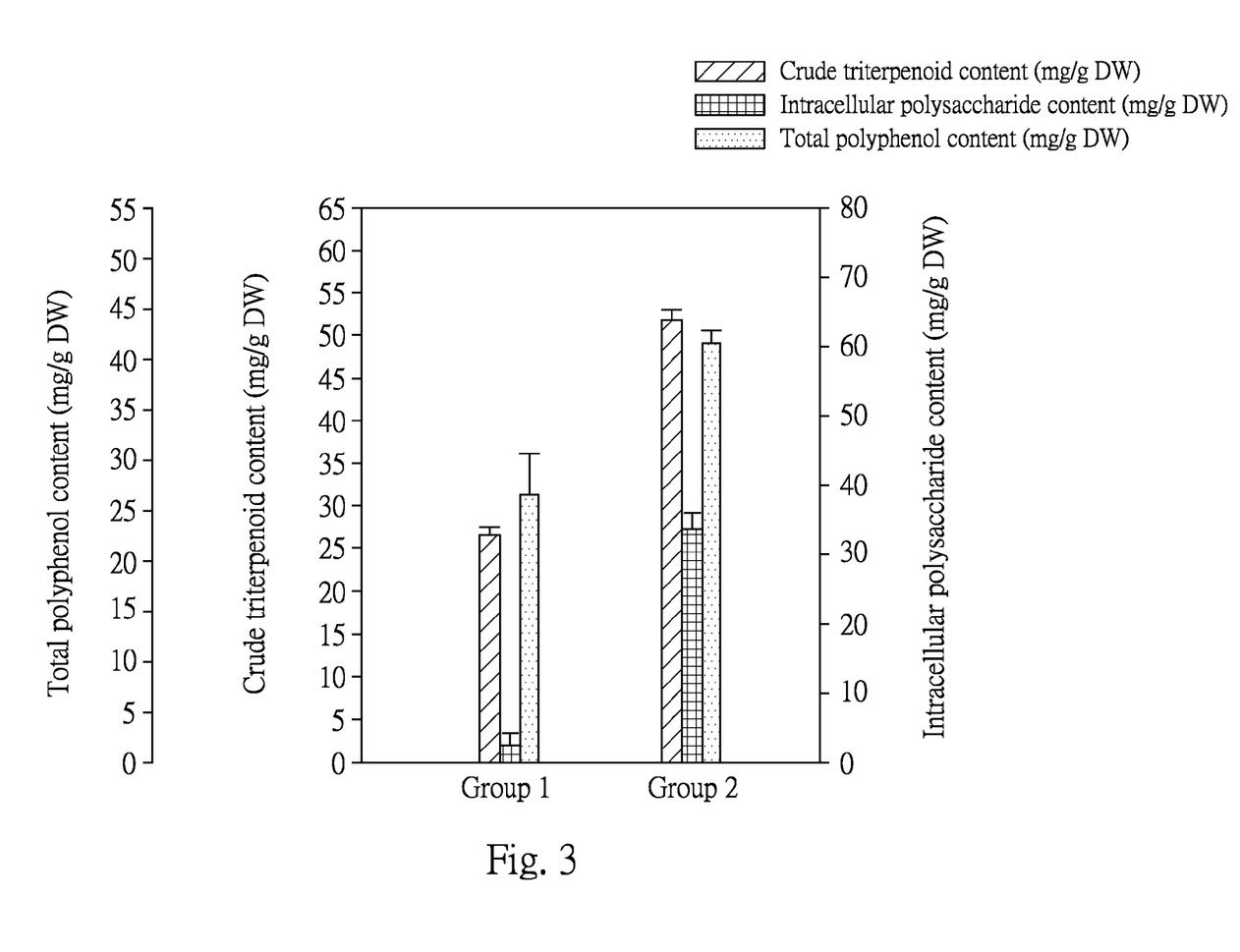
FIG. 3 is the results of the amounts of the bioactive components in the *Antrodia cinnamomes* cultured on the brown powder based medium with different water contents.

According to FIG. 3, it shows that the *Antrodia cinnamomea* cultured on the brown rice powder based medium which contains 55% water content comprises 2.42 mg/g intracellular polysaccharides, 46.38 mg/g polyphenols and 51.84 mg/g crude triterpenoid, and the *Antrodia cinnamomea* cultured on the brown rice powder based medium, which contains 45% water content comprises 33.55 mg/g intracellular polysaccharides, 41.60 mg/g polyphenols and 51.84 mg/g crude triterpenoid. Furthermore, it reveals that the amounts of bioactive components of *Antrodia cinnamomea* cultured on the 45% water content of brown rice powder based medium is higher than that cultured on the 55% water content containing of brown rice powder based medium.

Figure 4:
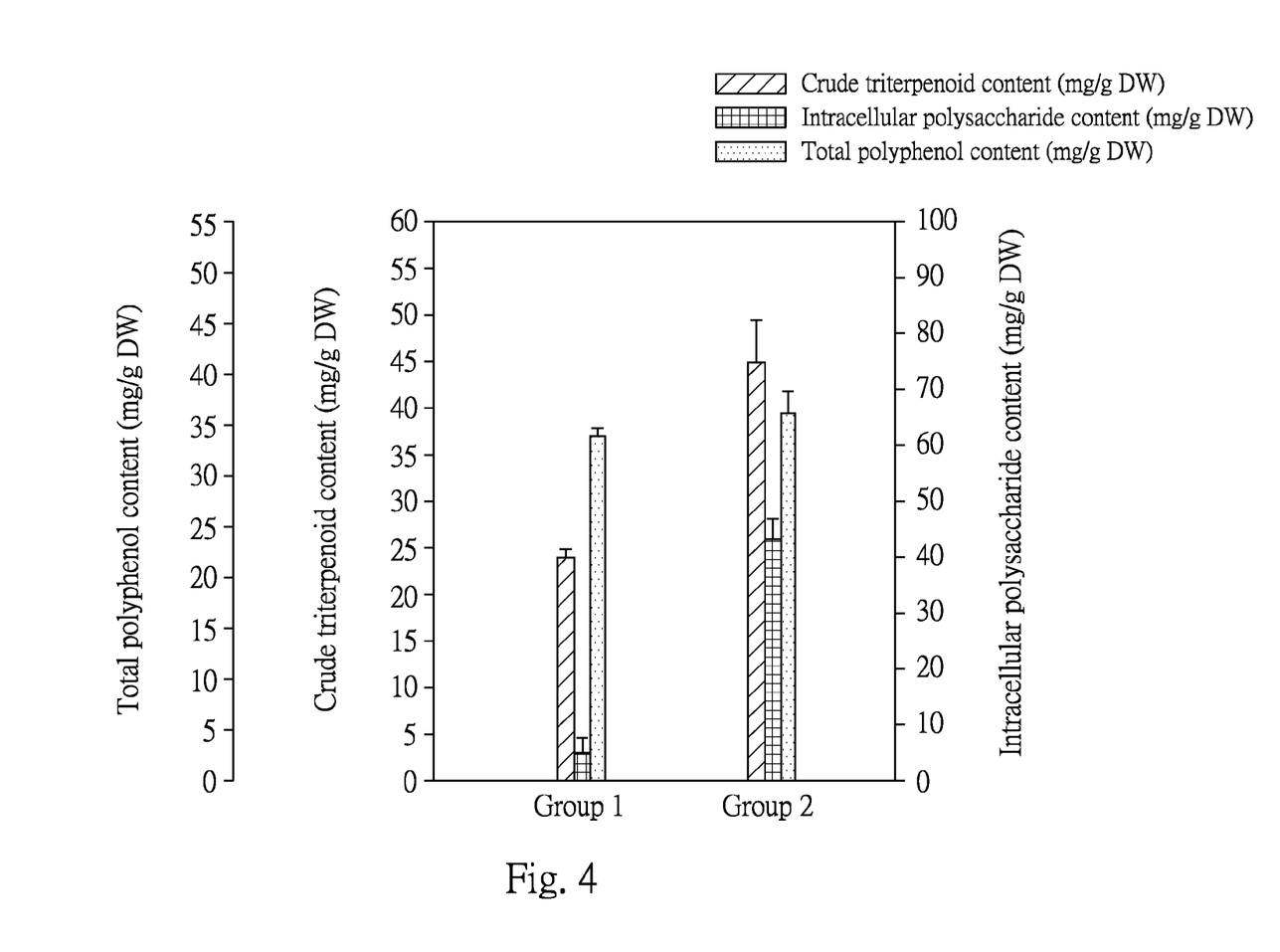
FIG. 4 is the results of the amounts of the bioactive components in the *Antrodia cinnamomes* cultured on the Tartary buckwheat flour based medium with different water contents.

FIG. 4 shows that the *Antrodia cinnamomea* cultured on the Tartary buckwheat flour based medium which contains 55% water content comprises 5.01 mg/g intracellular polysaccharides, 33.90 mg/g polyphenols and 23.95 mg/g crude triterpenoid. In addition, the *Antrodia cinnamomea* cultured on the Tartary buckwheat flour based medium which contains 45% water content comprises 43.02 mg/g intracellular polysaccharides, 36.27 mg/g polyphenols and 44.82 mg/g crude triterpenoid. Taken together, *Antrodia cinnamomea* cultured on the 45% water content of Tartary buckwheat flour based medium reveals higher amounts of bioactive components than that cultured on the 55% water content containing Tartary buckwheat flour based medium.

Figure 5:
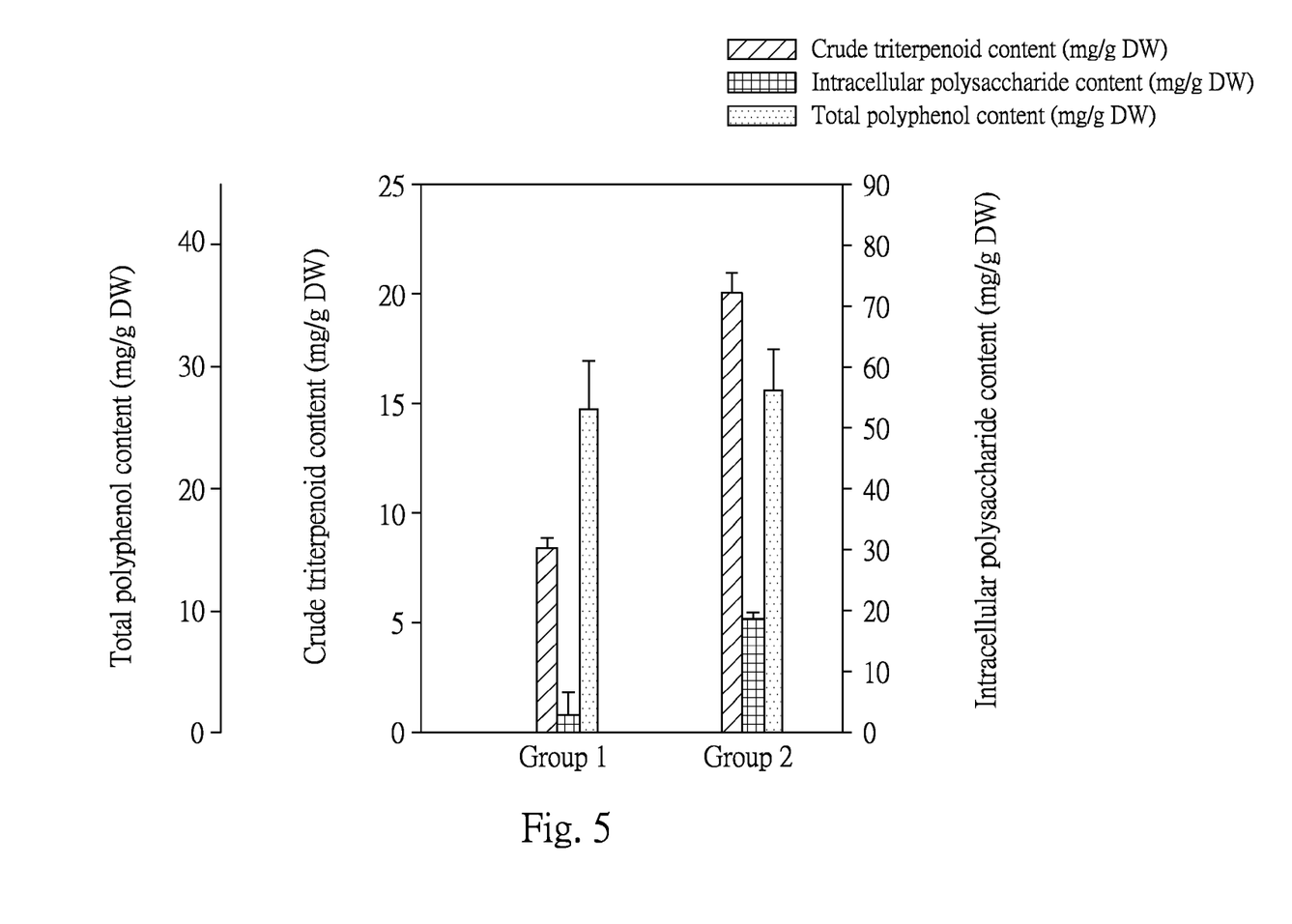
FIG. 5 is the results of the amounts of the bioactive components in the *Antrodia cinnamomes* cultured on the adlay powder based medium with different water contents.

FIG. 5 shows that the *Antrodia cinnamomea* cultured on 55% moisture content of adlay powder based medium comprises 2.84 mg/g intracellular polysaccharides, 26.53 mg/g polyphenols and 8.41 mg/g crude triterpenoid. In addition, the *Antrodia cinnamomea* cultured on 45% water content of adlay powder based medium comprises 18.70 mg/g intracellular polysaccharides, 28.20 mg/g polyphenols and 20.06 mg/g crude triterpenoid.

These results in FIG. 3 to FIG. 5 suggest that the *Antrodia cinnamomea* cultured on 45% water content of the medium produces more bioactive components than that cultured on 55% water content of the medium.

Example 7

The Effects of Culture Temperature

Figure 6:
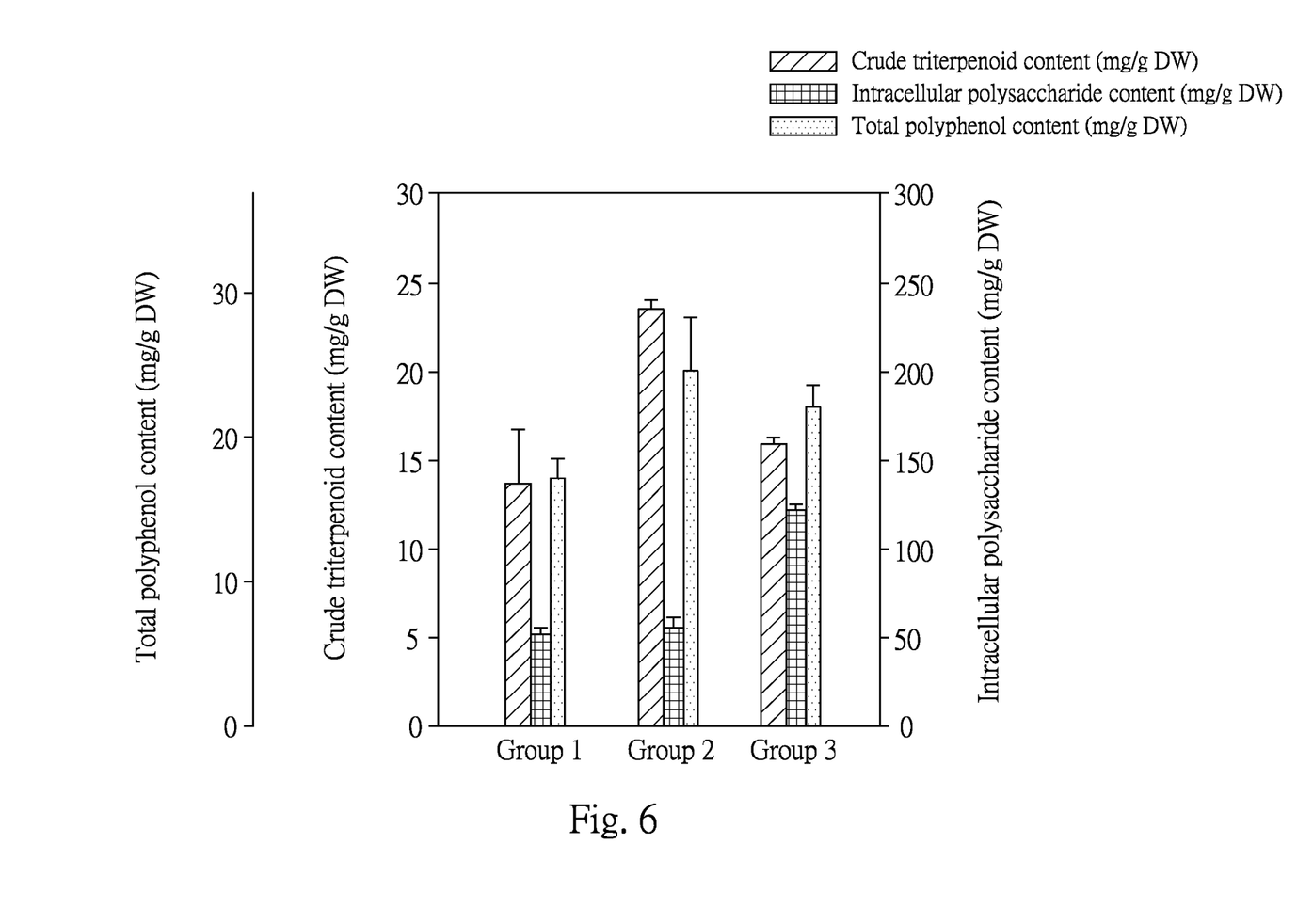
FIG. 6 is the results of the amounts of the bioactive components in the *Antrodia cinnamomes* cultured at different culture temperatures.

In this example, there were three experimental groups performed to determine the effect of culture temperature. In each experimental group, 25 g of grained brown rice powder was spread on the glass plate that was add with water to prepare the 45% water content of solid-state medium. After sterilization, the seed strain of *Antrodia cinnamomea* was spread on the medium with 5% inoculation rate, and cultured in the incubators with different temperature, wherein the group 1 is cultured in the incubator at 25° C. for 30 days; the group 2 is sequentially cultured at 25° C. for 15 days and then cultured at 30° C. for 15 days; and the group 3 is sequentially cultured at 30° C. for 15 days and then cultured at 35° C. for 15 days. After the culture at different temperature conditions, the *Antrodia cinnamomea* of each group was collected for the measurements of the bioactive components using the procedures indicated in examples 2~4. The results showed in FIG. 6 suggest that the *Antrodia cinnamomea* in the group 2 and the group 3 reveal increased amounts of bioactive components with comparison of the group 1.

In detail, the *Antrodia cinnamomea* in the group 2 reveals 23.27 mg/g polyphenol and 23.51 mg/g crude triterpenoid that are more than that in the group 1. In addition, the *Antrodia cinnamomea* in the group 3 reveals 121.26 mg/g intracellular polysaccharides that is more than that in the group 1. Therefore, the results in FIG. 6 suggest that *Antrodia cinnamomea* cultured at 30~35° C. will promote the production of bioactive components.

Furthermore, it is better to culture *Antrodia cinnamomea* at 30° C. for elevating the amounts of polyphenols and crude triterpenoid and to culture *Antrodia cinnamomea* at 35° C. for increasing the amounts of intracellular polysaccharides.

Example 8

The Effects of the Compositions of Solid-State Medium

The brown rice, Tartary buckwheat and adlay were grained into powders for the preparation of 45% water content containing mediums with different constituting ratios as 4 groups, wherein the medium of group 1 was composed of brown rice powder alone; the medium of group 2 was composed of brown rice powder, Tartary buckwheat flour and adlay powder with the ratio 5:2:1; the medium of group 3 was composed of brown powder, Tartary buckwheat flour and adlay powder with the ration 7:2:1; the medium of group 4 was composed of brown powder, Tartary buckwheat flour and adlay powder with the ration at 9:2:1. The media of each group was sterilized and spread the seed strain of *Antrodia cinnamomea* prepared in example 1 with 5% of inoculation rate for the following culture for 3 months.

Figure 7:
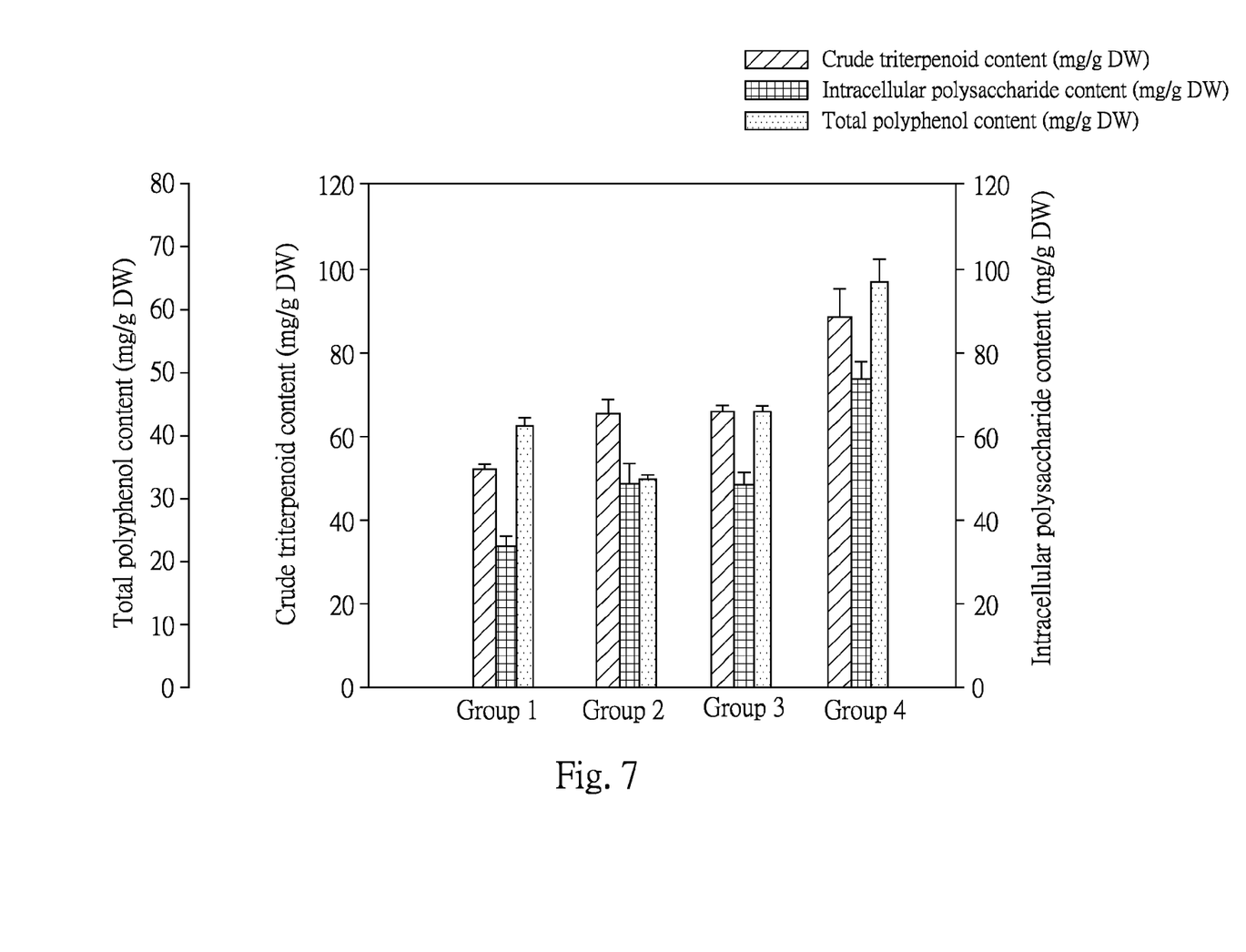
FIG. 7 is the results of the amounts of the bioactive components in the *Antrodia cinnamomes* cultured on solid-state culture medium composed of mixed grain with different ratios.

After culture for 3 months, the *Antrodia cinnamomea* growing on the media in each group was collected for the measurements of those indicated bioactive components by the procedures indicated in example 2~4. The results in this example are showed in FIG. 7. The FIG. 7 shows that the amounts of bioactive components in the *Antrodia cinnamomea* of group 4 are more than those of other three groups. These results indicate that the composition of the medium in the group 4 (brown rice powder:Tartary buckwheat flour: adlay powder=9:2:1) is capable of increasing the bioactive components of cultured *Antrodia cinnamomea*. In FIG. 7, the less ratio of adlay powder in the solid-state medium composed of brown powder, Tartary buckwheat flour and adlay powder will increase the amount of crude triterpenoid in the cultured *Antrodia cinnamomea*.

According to the examples and embodiments, the invention discloses the culture method for *Antrodia cinnamomea* to elevate the amount of bioactive components through modifications of the light source and intensity. Furthermore, the method accompanies with modification of other culture conditions such as two-stages culture temperature, composition and water content of medium are capable of increasing the bioactive components in *Antrodia cinnamomea*. Therefore, the culture method for *Antrodia cinnamomea* disclosed in the invention is capable of increasing the thickness of the fruiting bodies and elevating the amounts of bioactive components in *Antrodia cinnamomea*. The cultured *Antrodia cinnamomea* could be completely separated from the medium. The above advantages can increase the industry value and usage of the cultured *Antrodia cinnamomea*.

The above-mentioned specification is only for detailedly describing the examples of the invention and shall not be construed as a limitation of the scope of the invention Thus, any modification or change without departing from the characteristics of the invention or any equivalent thereof shall be included in the scope of the invention defined in the following claims.

What is claimed is:

1. A culture method for *Antrodia cinnamomea* inoculating a seed strain of *Antrodia cinnamomea* to a culture medium with at least one cultured condition, characterized in the culture condition including a light environment is selected from the group comprising of green light and blue light, and the seed strain of *Antrodia cinnamomea* is prepared by the homogenization of *Antrodia cinnamomea* mycelia.

2. The culture method for *Antrodia cinnamomea* according to claim 1, wherein the light intensity of the light environment is between 1 µmol/s·m$^2$ to 20 µmol/s·m$^2$.

3. The culture method for *Antrodia cinnamomea* according to claim 2, wherein the light intensity of blue light is between 2 µmol/s·m$^2$ to 16 µmol/s·m$^2$.

4. The culture method for *Antrodia cinnamomea* according to claim 2, wherein the light intensity of green light is between 11 µmol/s·m$^2$ to 20 µmol/s·m$^2$.

5. The culture method for *Antrodia cinnamomea* according to claim 1, wherein the culture condition further includes a culture temperature of 25° C.~35° C.

6. The culture method for *Antrodia cinnamomea* according to claim 1, wherein the culture medium comprises a powder matrix mixed with water in a predetermined ratio.

7. The culture method for *Antrodia cinnamomea* according to claim 6, wherein the powder matrix includes at least one cereal grain.

8. The culture method for *Antrodia cinnamomea* according to claim 7, wherein the powder matrix is selected from the group comprising of brown rice powder, Tartary buckwheat flour and adlay powder.

9. The culture method for *Antrodia cinnamomea* according to claim 8, wherein the powder matrix is composed of brown rice powder, Tartary buckwheat flour and adlay powder in a predetermined mixed ratio.

10. The culture method for *Antrodia cinnamomea* according to claim 9, wherein the contained amount of the powder matrix from low to high is sequentially adlay powder, Tartary buckwheat and brown rice powder.

11. The culture method for *Antrodia cinnamomea* according to claim 9, wherein the contained amount of the powder matrix from low to high is sequentially adlay powder, brown rice powder Tartary buckwheat flour.

12. The culture method for *Antrodia cinnamomea* according to claim 9, wherein the mixed ratio of the powder matrix is 1-fold of adlay powder, 10- to 2-fold brown rice powder and 2- to 10-fold Tartary buckwheat flour.

13. The culture method for *Antrodia cinnamomea* according to claim 12, wherein the mixed ratios of brown rice powder, Tartary buckwheat flour and adlay powder is 9:2:1.

14. The culture method for *Antrodia cinnamomea* according to claim 6, wherein the water content of the culture medium is 35~55%.

15. The culture method for *Antrodia cinnamomea* according to claim 14, wherein the water content of the culture medium is 35~50%.

16. The culture method for *Antrodia cinnamomea* according to claim 1, further includes two culture conditions, wherein one culture condition of culturing in dark for 15 days and another culture condition of culturing in the light environment at least for 15 days.

17. The culture method for *Antrodia cinnamomea* according to claim 16, wherein the temperature of the one culture condition is lower than that of the another culture condition.

18. The culture method for *Antrodia cinnamomea* according to claim 17, wherein the temperature of the one culture condition is 25° C. and the temperature of the another culture condition is 25~35° C.

* * * * *